(12) United States Patent
Hoyes et al.

(10) Patent No.: US 10,551,347 B2
(45) Date of Patent: Feb. 4, 2020

(54) METHOD OF ISOLATING IONS

(71) Applicant: Micromass UK Limited, Wilmslow (GB)

(72) Inventors: John Brian Hoyes, Stockport (GB);
Steven Derek Pringle, Darwen (GB);
Farnoush Salarzaei, Cheshire (GB);
Jason Lee Wildgoose, Stockport (GB)

(73) Assignee: MICROMASS UK LIMITED, Wilmslow (GB)

( * ) Notice: Subject to any disclaimer, the term of this patent is extended or adjusted under 35 U.S.C. 154(b) by 0 days.

(21) Appl. No.: 15/035,919

(22) PCT Filed: Nov. 11, 2014

(86) PCT No.: PCT/GB2014/053333
§ 371 (c)(1),
(2) Date: May 11, 2016

(87) PCT Pub. No.: WO2015/071647
PCT Pub. Date: May 21, 2015

(65) Prior Publication Data
US 2016/0274059 A1    Sep. 22, 2016

(30) Foreign Application Priority Data

Nov. 12, 2013  (EP) ..................................... 13192581
Nov. 12, 2013  (GB) .................................. 1319952.6

(51) Int. Cl.
*G01N 27/62*       (2006.01)
*H01J 49/40*       (2006.01)
(Continued)

(52) U.S. Cl.
CPC ........ *G01N 27/622* (2013.01); *H01J 49/0031* (2013.01); *H01J 49/40* (2013.01); *H01J 49/4215* (2013.01)

(58) Field of Classification Search
CPC ............... G01N 27/622; H01J 49/4215; H01J 49/0031; H01J 49/40
See application file for complete search history.

(56) References Cited

U.S. PATENT DOCUMENTS 6,960,761 B2    11/2005  Clemmer
7,095,014 B2    8/2006   Hoyes
(Continued)

FOREIGN PATENT DOCUMENTS

EP    1365438 A2 *  11/2003  ............ H01J 49/004
WO   2010/085720 A1   7/2010

*Primary Examiner* — Wyatt A Stoffa
*Assistant Examiner* — Sean M Luck

(57) ABSTRACT

A method of mass spectrometry is disclosed comprising isolating a group of different ions derived from chemical compounds in the same class, wherein the different ions have different mass to charge ratios and ion mobilities. The step of isolating comprises temporally separating the ions according to their ion mobility in an ion mobility separator; and mass filtering the ions according to mass to charge ratio with a mass filter. The mass to charge ratios transmitted by the mass filter are varied as a function of time such that said different ions derived from chemical compounds in the same class are transmitted by the mass filter and other ions are not transmitted by the mass filter.

23 Claims, 1 Drawing Sheet

(51) Int. Cl.
*H01J 49/42* (2006.01)
*H01J 49/00* (2006.01)

(56) References Cited

U.S. PATENT DOCUMENTS

| | | | |
|---|---|---|---|
| 7,586,088 B2 | 9/2009 | Bateman et al. | |
| 8,785,848 B2 | 7/2014 | Wu et al. | |
| 8,921,772 B2 | 12/2014 | Verentchikov | |
| 9,207,206 B2 | 12/2015 | Makarov | |
| 2002/0014586 A1* | 2/2002 | Clemmer | G01N 27/622 250/287 |
| 2004/0113064 A1* | 6/2004 | Fuhrer | G01N 27/622 250/287 |
| 2005/0035284 A1* | 2/2005 | Schultz | H01J 49/0031 250/287 |
| 2005/0109931 A1* | 5/2005 | Schultz | G01N 27/622 250/287 |
| 2005/0189486 A1* | 9/2005 | Fuhrer | G01N 27/622 250/287 |
| 2007/0069120 A1* | 3/2007 | Shvartsburg | G01N 27/624 250/287 |
| 2008/0149824 A1* | 6/2008 | Miller | G01N 27/624 250/287 |
| 2010/0108879 A1 | 5/2010 | Bateman et al. | |
| 2010/0200742 A1* | 8/2010 | Schultz | H01J 49/0045 250/252.1 |
| 2012/0138783 A1* | 6/2012 | Peng | G01N 27/622 250/282 |
| 2013/0187037 A1 | 7/2013 | Wu et al. | |
| 2015/0041636 A1 | 2/2015 | Giles et al. | |

\* cited by examiner

METHOD OF ISOLATING IONS

CROSS REFERENCE TO RELATED APPLICATIONS

This application is the National Stage of International Application No. PCT/GB2014/053333, filed 11 Nov. 2014 which claims priority from and the benefit of United Kingdom patent application No. 1319952.6 filed on 12 Nov. 2013 and European patent application No. 13192581.0 filed on 12 Nov. 2013. The entire contents of these applications are incorporated herein by reference.

BACKGROUND TO THE PRESENT INVENTION

The present invention provides a method of mass spectrometry and a mass spectrometer for isolating different ions derived from chemical compounds in the same chemical class.

Various methods are know in mass spectrometry for separating one type of ion from other ions prior to analysis. For example, a mass filter may be used to mass selectively transmit only one type of ion in order to isolate a desired type of ion. Alternatively, an ion mobility separator may be used to separate ions from each other according to their ion mobilities.

However, it is desired to provide a convenient way to isolate a group of different ions derived from chemical compounds in the same chemical class.

It is therefore desired to provide an improved method of mass spectrometry and an improved mass spectrometer.

SUMMARY OF THE PRESENT INVENTION

From a first aspect the present invention provides a method of mass spectrometry comprising:

isolating a group of different ions derived from chemical compounds in the same class, wherein said different ions have different mass to charge ratios and ion mobilities, and wherein said step of isolating comprises:
 (i) obtaining a known relationship, or determining a relationship between the mass to charge ratios and the ion mobilities of said different ions derived from chemical compounds in the same class;
 (ii) temporally separating the ions according to their ion mobility in an ion mobility separator; and then
 (iii) mass filtering the resulting separated ions according to mass to charge ratio with a mass filter, wherein the mass to charge ratios transmitted by the mass filter are varied with time as a function of the ion mobilities received at the mass filter from the ion mobility separator and according to said relationship such that said different ions derived from chemical compounds in the same class are transmitted by the mass filter and other ions are not transmitted by the mass filter;

wherein said method further comprises removing the temporal separation of ions after they have been separated and mass filtered, and then mass analysing the ions or ions derived therefrom.

The present invention provides a convenient and efficient method of isolating a group of different ions derived from chemical compounds in the same class. Other ions are removed, rendering detection and mass analysis of said different ions particularly efficient.

The mass filter is varied with time such that ions derived from different chemical compounds that are in the same chemical class are preferably substantially isolated from all other ions. Ions not from said chemical class are preferably not transmitted.

It is known to selectively transmit ions having desired combinations of ion mobility and mass to charge ratio for the purpose of charge state selection, for example, from EP 1365438. However, EP 1365438 does not recognise that compounds in the same chemical class have ion mobilities and mass to charge ratios that follow a relationship. As such, this document does not disclose or suggest the concept of isolating a group of different ions derived from chemical compounds in the same class.

US 2002/014586 discloses in general the features of separating ions by ion mobility and mass filtering ions. However, this document also does not disclose or suggest the concept of isolating a group of different ions derived from chemical compounds in the same class.

The term "ions derived from chemical compounds in the same class" is preferably intended to mean ionised chemical compounds in the same class. Said different ions are preferably produced by ionising an analyte and are not fragment ions.

For the avoidance of doubt, the group of different ions is a group of different types of ions.

Preferably, said class of chemical compounds corresponds to compounds that share one or more common functional group or share a common moiety. The class of chemical compounds preferably corresponds to compounds that share one or more common functional group or share a common moiety such that the one or more functional group or moiety provides the compounds with similar chemical reactivity or with a common chemical property.

The compounds in said class of compounds preferably have a common functional group or moiety that defines said class of compounds.

Preferably, each of said different ions includes said one or more functional group or said moiety.

Said class of compounds is preferably one of: lipids; pesticides; metabolites; peptides; proteins; antibodies; enzymes; a class of compounds with related biological function or activity; a class of compounds with related chemical structure; a class of compounds with related chemical reactivity; or a class of compounds with related solution chemistry.

Preferably, substantially only ions derived from said chemical compounds in the same class of compounds are transmitted by the mass filter and all other ions are not transmitted by the mass filter and are rejected.

The mass filter transmits said different ions derived from chemical compounds in the same class and filters out other ions, wherein said other ions preferably have the same charge state as at least some of said different ions that are transmitted by the mass filter.

Said group of different ions derived from chemical compounds in the same class may initially be intermixed with other ions that are not derived from said chemical compounds in the same class. At least some of said other ions may have the same charge state as at least some of said ions derived from chemical compounds in the same class. The mass to charge ratios transmitted by the mass filter are preferably varied with time as a function of the ion mobilities received at the mass filter from the ion mobility separator and according to said relationship such that said other ions are not transmitted by the mass filter but said ions derived from chemical compounds in the same class having the same charge state as said other ions are transmitted by the mass filter.

For example, said other ions may be background matrix ions that have the same charge state as at least some of the ions derived from chemical compounds in the same class. At least some of said ions derived from chemical compounds in the same class are preferably singly charged ions and/or said other ions are preferably singly charged ions.

Preferably, said different ions derived from chemical compounds in the same class consist of or comprise singly charged ions and said other ions also consist of or comprise singly charged ions.

Preferably, the mass to charge ratios of said different ions vary as a function of their ion mobilities such that the ions from the same class of chemical compounds follow a trend; and wherein the mass to charge ratios transmitted by the mass filter vary with time so as to follow said trend and thereby transmit the ions from the same class of chemical compound and filter out other ions.

The relationship between the mass to charge ratios and the ion mobilities of said different ions may be such that the mass to charge ratios of the ions increase substantially continuously with increasing ion mobility.

The mass to charge ratios of said different ions derived from chemical compounds in the same class may vary as a substantially linear or polynomial function of their ion mobility.

The mass filter may be operated so as to only transmit ions having a mass to charge ratio greater than a minimum value and a mass to charge ratio less than a maximum value, and the mass filter may be is scanned with time so that said minimum value and said maximum value are progressively increased with time. The mass filter may be scanned in a continuous or in a stepped manner.

Preferably, said different ions are mass analysed after they have been transmitted by the mass filter. The mass analyser may comprise a detector that detects the ions.

The temporal separation of the different ions is preferably removed by transmitting the separated and mass filtered ions into a region comprising a collisional gas such that the ions collide with the gas and said different ions intermix.

By removing the temporal separation of the ions after the mass filtering, the preferred embodiment counteracts the loss in dynamic range of the instrument that would otherwise be associated with the temporal compression or concentration of the ion populations introduced by the ion mobility separator. This is a particular issue when a time of Flight (ToF) mass analyser is arranged downstream of the mass filter, as the dynamic range of the instrument is already restricted by the detection system of the ToF mass analyser. Accordingly, the mass analyser used in the present invention may be a ToF mass analyser. Removing the temporal separation also removes the data storage requirements of the instrument as the ion mobility data is no longer stored.

Ions are preferably pulsed into the ion mobility separator (IMS) and the IMS device may perform a separation cycle on each group of ions pulsed into the IMS device. The mass to charge ratio transmission window of the mass filter is preferably scanned during each IMS device cycle so as to selectively filter ions.

Preferably, the range of mass to charge ratios transmitted by the mass filter at any given drift time is smaller than the range of mass to charge ratios that is within the mass filter at that drift time.

A Time of Flight mass analyser is preferred and the present invention may be employed in combination with other established Time of Flight enhancements such as EDC/HDC. However, it is also contemplated that types of mass analyser other than a Time of Flight mass analyser may be used in the present invention. For example, an analytical quadrupole mass analyser with ion detector may replace the Time of Flight mass analyser in an IMS-Q-Q arrangement.

Ions may be pulsed into the ion mobility separator a plurality of times. A first pulse of ions may be pulsed into the ion mobility separator and the ions separated therein and a second pulse of ions may be subsequently pulsed into the ion mobility separator and the ions separated therein. The mass to charge ratios of the ions transmitted by the mass filter may vary as a function of ion mobility separator drift time according to a first function for the ions from the first ion pulse, and may vary as a second different function for the ions from the second pulse. Third or further pulses of ions may be provided and the mass filter may vary according to a third or further function respectively.

The mass filter may comprise an RF quadrupole and a DC resolving voltage. Less preferably, the mass filter may be an RF only quadrupole having a low mass cut off that acts as the mass filter.

Although a quadrupole mass filter is primarily described herein, other types of mass filter are contemplated for performing the same function. For example, less preferably, the ions may be received from the ion mobility separator in an ion trap and the ion trap may subsequently mass selectively eject ions into the collision cell. The ion trap therefore mass filters the ions that reach the collision cell. Alternative types of less preferred filter are also contemplated, such as the use of a time of flight device that separates ions according to their time of flight and transmits only ions having selected flight times.

Although it has been described that the precursor ions are separated by ion mobility separation through a gas, it is contemplated that the ions may alternatively be separated according to Field Asymmetric Ion Mobility Separation (FAIMS), or according to a physico-chemical property other than ion mobility or FAIMS.

Preferably, the ions are transmitted from the mass filter to a mass analyser for performing said mass analysing without being trapped in an ion trap. The ions may be radially confined, but are preferably not trapped in three dimensions.

The method may be operated in a first mode so that at least some of the ions transmitted by the mass filter are fragmented or reacted so as to produce fragment or product ions, and said step of mass analysing may comprise mass analysing the fragment or product ions.

The method may also be operated in a second mode so that at least some of the ions transmitted by the mass filter are not fragmented or reacted, and said step of mass analysing comprises mass analysing the precursor ions transmitted by the mass filter.

The method may be repeatedly alternated between the first and second modes whilst said ions derived from chemical compounds in the same class are being temporally separated in the ion mobility separator and as these ions elute from the ion mobility separator.

Preferably, the fragment or product ions that are mass analysed and detected in the first mode are associated with the elution times at which their respective precursor ions eluted from the ion mobility separator; the precursor ions that are mass analysed and detected in the second mode are associated with their elution times from the ion mobility separator; and the fragment or product ions detected in the first mode are associated with their respective precursor ions detected in the second mode by matching the elution times associated with the fragment or product ions with the elution times associated with the precursor ions.

The method preferably further comprises identifying a precursor ion from one or more fragment or product ion determined to be associated with the precursor ion.

The present invention also provides a mass spectrometer arranged and configured to perform any one of the methods described herein.

Accordingly, the present invention provides a mass spectrometer comprising:

means for isolating a group of different ions derived from chemical compounds in the same class, wherein said different ions have different mass to charge ratios and ion mobilities; wherein said means for isolating comprises:
  (i) storage means for storing a relationship between the mass to charge ratios and the ion mobilities of said different ions derived from chemical compounds in the same class;
  (ii) an ion mobility separator for temporally separating the ions according to their ion mobility;
  (iii) a mass filter arranged downstream of the ion mobility separator for mass filtering the separated ions according to mass to charge ratio; and
  (iv) a controller arranged and configured to vary the mass to charge ratios transmitted by the mass filter with time as a function of the ion mobilities received at the mass filter from the ion mobility separator and according to said relationship such that said different ions derived from chemical compounds in the same class are transmitted by the mass filter and other ions are not transmitted by the mass filter; and
wherein said spectrometer further comprises means for removing the temporal separation of ions, said means being arranged downstream of the mass filter; and
a mass analyser for mass analysing ions.

It is contemplated herein that the method need not necessarily comprise the step of removing the temporal separation of ions after they have been separated and mass filtered.

Accordingly, from a second aspect the present invention provides a method of mass spectrometry comprising:

isolating a group of different ions derived from chemical compounds in the same class, wherein said different ions have different mass to charge ratios and ion mobilities, and wherein said step of isolating comprises:
  (i) obtaining a known relationship, or determining a relationship between the mass to charge ratios and the ion mobilities of said different ions derived from chemical compounds in the same class;
  (ii) temporally separating the ions according to their ion mobility in an ion mobility separator; and then
  (iii) mass filtering the resulting separated ions according to mass to charge ratio with a mass filter, wherein the mass to charge ratios transmitted by the mass filter are varied with time as a function of the ion mobilities received at the mass filter from the ion mobility separator and according to said relationship such that said different ions derived from chemical compounds in the same class are transmitted by the mass filter and other ions are not transmitted by the mass filter.

The second aspect of the present invention also provides a mass spectrometer comprising:

means for isolating a group of different ions derived from chemical compounds in the same class, wherein said different ions have different mass to charge ratios and ion mobilities; wherein said means for isolating comprises:
  (i) storage means for storing a relationship between the mass to charge ratios and the ion mobilities of said different ions derived from chemical compounds in the same class;
  (ii) an ion mobility separator for temporally separating the ions according to their ion mobility;
  (iii) a mass filter arranged downstream of the ion mobility separator for mass filtering the separated ions according to mass to charge ratio; and
  (iv) a controller arranged and configured to vary the mass to charge ratios transmitted by the mass filter with time as a function of the ion mobilities received at the mass filter from the ion mobility separator and according to said relationship such that said different ions derived from chemical compounds in the same class are transmitted by the mass filter and other ions are not transmitted by the mass filter.

The method and spectrometer according to the second aspect of the present invention may have any one or combination of preferred or optional features described herein in relation to the first aspect of the present invention.

The mass spectrometers disclosed herein may comprise:
  (a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; and (xxvi) a Solvent Assisted Inlet Ionisation ("SAII") ion source; and/or
  (b) one or more continuous or pulsed ion sources; and/or
  (c) one or more ion guides; and/or
  (d) one or more ion mobility separation devices and/or one or more Field Asymmetric Ion Mobility Spectrometer devices; and/or
  (e) one or more ion traps or one or more ion trapping regions; and/or
  (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic or orbitrap mass analyser; (x) a Fourier Transform electrostatic or orbitrap mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may comprise either:

(i) a C-trap and an Orbitrap® mass analyser comprising an outer barrel-like electrode and a coaxial inner spindle-like electrode, wherein in a first mode of operation ions are transmitted to the C-trap and are then injected into the Orbitrap® mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the Orbitrap® mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The mass spectrometer may comprises a device arranged and adapted to supply an AC or RF voltage to the electrodes. The AC or RF voltage preferably has an amplitude selected from the group consisting of: (i)<50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage preferably has a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

BRIEF DESCRIPTION OF THE DRAWINGS

Various embodiments of the present invention will now be described, by way of example only, and with reference to the accompanying drawings in which.

DETAILED DESCRIPTION OF PREFERRED EMBODIMENT

Figure 1:
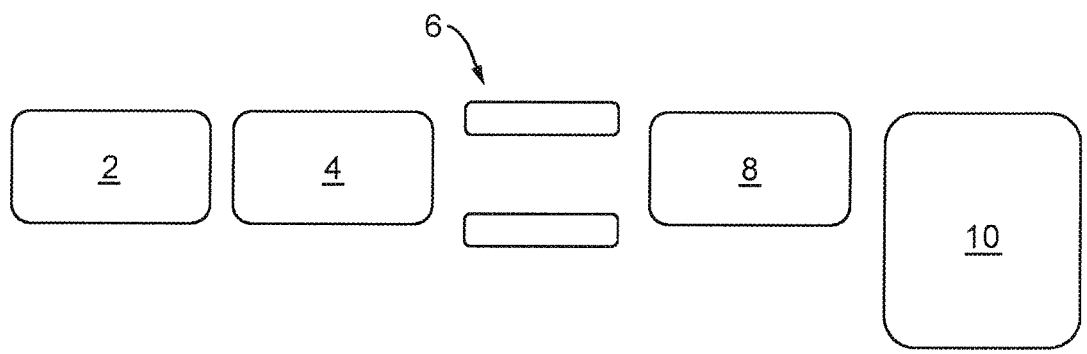
FIG. 1 shows a schematic of a mass spectrometer according to a preferred embodiment of the present invention.

FIG. 1 shows a schematic of a preferred embodiment of the present invention. This embodiment comprises an ion source 2, an ion mobility separator (IMS) 4, a quadrupole mass filter 6, a collision cell 8 and a Time of Flight mass analyser 10.

In operation, ions are generated by the ion source 2 and are directed into the IMS device 4. Ions having different mobilities pass through the gas in the IMS device 4 with different drift times and so the IMS device 4 causes the ions to separate according to their ion mobility through the IMS device 4. The quadrupole mass filter 6 is arranged between the IMS device 4 and the collision cell 8 and only transmits ions having a restricted range of mass to charge ratios at any given time. The mass to charge ratio transmission window of the quadrupole mass filter 6 is scanned with time whilst the ions emerge from the IMS device 4 such that the mass filter 6 mass selectively transmits ions from the IMS device 4 to the collision cell 8.

The mass filter 6 is scanned with time as a function of the drift time of the ions through the IMS device 4. As such, only ions having a selected combination of ion mobility and mass to charge ratio are transmitted through the mass filter 6. Different ions belonging to the same chemical class of compounds tend to have mass to charge ratios and ion mobilities that follow a common trend. The mass to charge ratios transmitted by the mass filter 6 are varied as a function of drift time through the IMS device 4 so as to follow this trend and only transmit ions in that class of chemical compounds. This enables target ions to be selectively filtered from other ions, such as background matrix ions, that may have the same charge state. Examples of target ions according to the preferred embodiments are singly charged lipids, metabolites & pesticides.

Figure 2A:
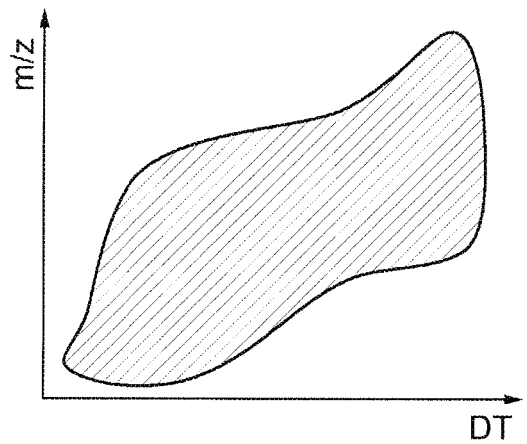
FIG. 2A is a plot showing the ion distribution entering the mass filter of FIG. 1.

FIG. 2A illustrates the mass to charge ratios of the ions leaving the IMS device 4 and passing into the quadrupole mass filter 6 as a function of drift time through the IMS device 4. It will be observed that ions having a relatively wide range of mass to charge ratios exit the IMS device 4 at any given drift time.

Figure 2B:
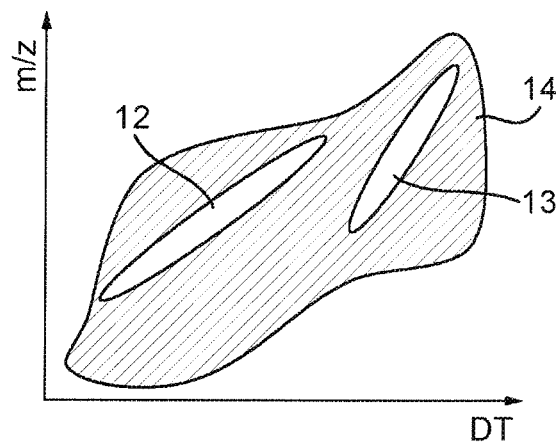
FIG. 2B is a plot showing the ion distribution leaving the mass filter of FIG. 1.

FIG. 2B shows two regions 12,13 that represent plots of the mass to charge ratios of ions transmitted by the quadrupole mass filter 6, as a function of their drift times through the IMS device 4. The area 14 surrounding the two regions 12,13 represents the ion distribution entering the mass filter 6, which is the same as the distribution of ions leaving the IMS device 4 and which is shown in FIG. 2A. It will be observed from FIG. 2B that the mass filter 6 mass selectively transmits only a relatively narrow range of mass to charge ratios at any given drift time. The mass filter 6 is varied with drift time so as to substantially only transmit ions from the chemical class of compounds that is of interest and to filter out other ions. For example, the mass filter 6 may be varied with time so as to substantially only transmit ions having a combination of IMS drift time and mass to charge ratio that correspond to pesticide ions, lipid ions or metabolite ions.

According to the embodiment in FIG. 2B, the mass to charge ratios transmitted by the mass filter 6 increase with drift time to pass a first band of ions that is shown as region 12. The mass to charge ratios transmitted by the mass filter 6 is then varied in a discontinuous manner such that the mass filter 6 begins transmitting mass to charge ratios in a second band of ions that is shown as the region 13. This allows the mass filter 6 to transmit ions that follow two different trends of mass to charge ratio and ion mobility.

After the mass filtering stage the temporal fidelity of the ions separated by the IMS device 4 is deliberately lost or compromised by colliding the ions with gas in the collision cell 8. In this first mode of operation the ions are not fragmented in the collision cell 8. Rather, the collision cell 8 acts to temporally spread the filtered ions so that the previously separated ions intermix. The ions are then mass analysed in the ToF mass analyser 10. This temporal spreading of the ions prior to mass analysis improves the dynamic range of the instrument, as it effectively undoes the temporal compression or concentration of the ion population that the IMS device 4 imposes on the ions. In addition, the loss of IMS fidelity and information negates the need to acquire the IMS drift time data and thereby reduces sizes of the data files that are stored.

A second mode of operation is also contemplated in which the ions are fragmented in the collision cell 8, e.g. via collisionally induce dissociation. In this mode the resulting fragment ions are analysed in the ToF mass analyser 10. The fragmentation device 8 may be repeatedly alternated between the first mode in which no fragmentation takes place and the second mode, such as in an $MS^e$ experiment. The ion signal profile for the precursor ions varies as a function of the drift time through the IMS device 4. The ion signal profile for a fragment ion can be matched to the ion signal profile for the precursor ions. This enables a fragment ion to be associated with an IMS drift time of its related precursor ion. As the mass filter 6 mass selectively transmits precursor ions as a function of IMS drift time, the IMS drift time that is associated with the fragment ion can be used to determine the mass to charge ratio of the precursor ion that is associated with the fragment ion. The precursor ion associated with the fragment ion can therefore be identified with confidence.

In the second mode of operation, the precursor ions may be induced to fragment in the fragmentation device 8 by accelerating the ions into the fragmentation device 8 with sufficient energy such that the ions interact with a gas in the fragmentation device 8 and fragment. Less preferably, the precursor ions may be induced to oscillate within a collision gas arranged in the fragmentation device 8 such that the precursor ions fragment. Precursor ions having different drift times through the ion mobility separator 4 may be subjected to different fragmentation energies so as to cause them to fragment. For example, precursor ions having a first IMS drift time may be accelerated into the fragmentation device 8 with a first energy or using a first acceleration voltage difference such that the ions fragment in the fragmentation device 8; and precursor ions having a second IMS drift time may be accelerated into the fragmentation device 8 with a second, different energy or using a second different acceleration voltage difference such that the ions fragment in the fragmentation device 8. If ions are induced to oscillate so as to fragment them then precursor ions having a first IMS drift time may be caused to oscillate into fragmentation by an oscillating electric field having a first frequency and/or amplitude, and precursor ions having a second IMS drift time may be caused to oscillate into fragmentation by an oscillating electric field having a second frequency and/or amplitude. Other methods of fragmentation are also contemplated. It is also contemplated that instead of fragmenting the ions, or in addition, the ions may be reacted with other molecules or ions so as to form product ions.

Although the present invention has been described with reference to preferred embodiments, it will be understood by those skilled in the art that various changes in form and detail may be made without departing from the scope of the invention as set forth in the accompanying claims.

The invention claimed is:

1. A method of mass spectrometry comprising:
   isolating a group of different ions derived from chemical compounds in the same class from other ions not derived from the chemical compounds in said same class, wherein said different ions have different mass to charge ratios and ion mobilities, and wherein said step of isolating comprises:
   (i) obtaining a known relationship, or determining a relationship between the mass to charge ratios and the ion mobilities of said different ions derived from chemical compounds in the same class;
   (ii) temporally separating ions according to their ion mobility in an ion mobility separator; and then
   (iii) mass filtering the resulting separated ions according to mass to charge ratio with a mass filter, wherein the mass to charge ratios transmitted by the mass filter are varied with time as a function of the ion mobilities received at the mass filter from the ion mobility separator and according to said relationship such that only ions of said different ions derived from chemical compounds in the same class are transmitted by the mass filter and said other ions not derived from the chemical compounds in the same class are not transmitted by the mass filter;
   wherein said method further comprises removing the temporal separation of ions after they have been separated and mass filtered, and then mass analysing the ions or ions derived therefrom.

2. The method of claim 1, wherein said class of chemical compounds corresponds to compounds that share one or more common functional group or share a common moiety.

3. The method of claim 2, wherein said class of chemical compounds corresponds to compounds that share one or more common functional group or share a common moiety such that the one or more functional group or moiety provides the compounds with similar chemical reactivity or with a common chemical property.

4. The method of claim 2, wherein each of said different ions includes said one or more functional group or said moiety.

5. The method of claim 1, wherein said class of compounds is one of: lipids, pesticides; metabolites; peptides; proteins; antibodies; enzymes; a class of compounds with related biological function or activity; a class of compounds with related chemical structure; a class of compounds with related chemical reactivity; or a class of compounds with related solution chemistry.

6. The method of claim 1, wherein said other ions that are not transmitted by the mass filter have the same charge state as at least some of said different ions that are transmitted by the mass filter.

7. The method of claim 1, wherein said group of different ions derived from chemical compounds in the same class are initially intermixed with said other ions that are not derived from said chemical compounds in the same class, at least some of said other ions have the same charge state as at least some of said ions derived from chemical compounds in the same class, and the mass to charge ratios transmitted by the mass filter are varied with time as a function of the ion mobilities received at the mass filter from the ion mobility separator and according to said relationship such that said other ions are not transmitted by the mass filter but said ions derived from chemical compounds in the same class having the same charge state as said other ions are transmitted by the mass filter.

8. The method of claim 6, wherein said different ions derived from chemical compounds in the same class consist of or comprise singly charged ions and said other ions also consist of or comprise singly charged ions.

9. The method of claim 1, wherein the relationship between the mass to charge ratios and the ion mobilities of said different ions is such that the mass to charge ratios of the ions increase substantially continuously with increasing ion mobility.

10. The method of claim 1, wherein the mass to charge ratios of said different ions derived from chemical compounds in the same class vary as a substantially linear or polynomial function of their ion mobility.

11. The method of claim 1, wherein the temporal separation of the different ions is removed by transmitting the separated and mass filtered ions into a region comprising a collisional gas such that the ions collide with the gas and said different ions intermix.

12. The method of claim 1, wherein said step of mass analysing is performed with a time of Flight mass analyser.

13. The method of claim 1, wherein the ions are transmitted from the mass filter to a mass analyser for performing said mass analysing without being trapped in an ion trap.

14. The method of claim 1, wherein the mass filter is a multipole mass filter, such as a quadrupole mass filter.

15. The method of claim 1, wherein in a first mode of operation at least some of the ions transmitted by the mass filter are fragmented or reacted so as to produce fragment or product ions, and said step of mass analysing comprises mass analysing the fragment or product ions.

16. The method of claim 15, wherein in a second mode of operation at least some of the ions transmitted by the mass filter are not fragmented or reacted, and said step of mass analysing comprises mass analysing the precursor ions transmitted by the mass filter.

17. The method of claim 16, wherein the method is repeatedly alternated between the first and second modes whilst said ions derived from chemical compounds in the same class are being temporally separated in the ion mobility separator and as these ions elute from the ion mobility separator.

18. The method of claim 16, wherein the fragment or product ions that are mass analysed and detected in the first mode are associated with the elution times at which their respective precursor ions eluted from the ion mobility separator; wherein the precursor ions that are mass analysed and detected in the second mode are associated with their elution times from the ion mobility separator; and wherein the fragment or product ions detected in the first mode are associated with their respective precursor ions detected in the second mode by matching the elution times associated with the fragment or product ions with the elution times associated with the precursor ions.

19. The method of claim 18, further comprising identifying a precursor ion from one or more fragment or product ion determined to be associated with the precursor ions.

20. A mass spectrometer arranged and configured to perform the method of claim 1.

21. A mass spectrometer comprising:
an ion mobility separator;
a mass filter arranged downstream of the ion mobility separator; and
a mass analyser;
wherein said mass spectrometer is configured to:
isolate a group of different ions derived from chemical compounds in the same class from other ions not derived from the chemical compounds in said same class, wherein said different ions have different mass to charge ratios and ion mobilities, by:
  (i) storing a relationship between the mass to charge ratios and the ion mobilities of said different ions derived from chemical compounds in the same class;
  (ii) temporally separating ions according to their ion mobility in the ion mobility separator; and then
  (iii) mass filtering the resulting separated ions according to mass to charge ratio with the mass filter, wherein
  (iv) the mass to charge ratios transmitted by the mass filter are varied with time as a function of the ion mobilities received at the mass filter from the ion mobility separator and according to said relationship such that only ions of said different ions derived from chemical compounds in the same class are transmitted by the mass filter and said other ions not derived from the chemical compounds in the same class are not transmitted by the mass filter;
wherein said mass spectrometer is further configured to remove the temporal separation of ions after they have been separated and mass filtered, and then mass analyse the ions or ions derived therefrom with the mass analyser.

22. The method of claim 1, wherein the mass filter to only transmit ions having a mass to charge ratio greater than a minimum value and a mass to charge ratio less than a maximum value, wherein the mass filter is scanned with time so that said minimum value and said maximum value vary with time.

23. The method of claim 1, wherein said step of mass filtering comprises mass filtering ions comprising both said ions derived from chemical compounds in the same class and said other ions not derived from the chemical compounds in said same class such that only said ions derived from chemical compounds in the same class are transmitted by the mass filter and said other ions not derived from the chemical compounds in the same class are not transmitted by the mass filter.

\* \* \* \* \*